United States Patent
Tamminga et al.

(10) Patent No.: US 10,413,052 B2
(45) Date of Patent: Sep. 17, 2019

(54) METHODS AND SYSTEMS FOR ORAL CLEANING DEVICE LOCALIZATION

(71) Applicant: KONINKLIJKE PHILIPS N.V., Eindhoven (NL)

(72) Inventors: Stephanus Jacob Gerardus Tamminga, Groningen (NL); Dionisio Massingo Nunes, Groningen (NL)

(73) Assignee: KONINKLIJKE PHILIPS N.V., Eindhoven (NL)

(*) Notice: Subject to any disclaimer, the term of this patent is extended or adjusted under 35 U.S.C. 154(b) by 0 days.

(21) Appl. No.: 15/557,531

(22) PCT Filed: Oct. 8, 2016

(86) PCT No.: PCT/IB2016/056039
§ 371 (c)(1),
(2) Date: Sep. 12, 2017

(87) PCT Pub. No.: WO2017/068453
PCT Pub. Date: Apr. 27, 2017

(65) Prior Publication Data
US 2018/0279763 A1    Oct. 4, 2018

Related U.S. Application Data

(60) Provisional application No. 62/244,338, filed on Oct. 21, 2015.

(51) Int. Cl.
*A46B 15/00* (2006.01)
*A61C 17/22* (2006.01)
*A61C 1/00* (2006.01)

(52) U.S. Cl.
CPC ...... *A46B 15/0006* (2013.01); *A46B 15/0004* (2013.01); *A46B 15/0008* (2013.01); *A61C 1/0015* (2013.01); *A61C 17/221* (2013.01)

(58) Field of Classification Search
CPC ............ A46B 15/0006; A46B 15/0004; A46B 15/0008; A61C 1/0015; A61C 17/221
See application file for complete search history.

(56) References Cited

U.S. PATENT DOCUMENTS 6,536,068 B1 * 3/2003 Yang ................. A46B 15/0002
15/105
8,176,591 B2    5/2012 Iwahori et al.
(Continued)

FOREIGN PATENT DOCUMENTS

CN      204501067      7/2015
GB      2519579 A      4/2015
(Continued)

OTHER PUBLICATIONS

Fitt's Law, Downloaded From Wikipedia, on Sep. 11, 2017, 6 Page Document.

*Primary Examiner* — Joseph J Hail
*Assistant Examiner* — J Stephen Taylor

(57) ABSTRACT

A method (300) for localizing an oral cleaning device within a user's mouth. The method includes the steps of: (i) determining (830), based on sensor information received from a motion identifier (28), a first location of the oral cleaning device within the user's mouth; (ii) measuring (850), using sensor information received from the motion identifier, an amount of time elapsing between a start and a stop of a movement of the oral cleaning device within the user's mouth at the first location; (iii) calculating (850), using Fitt's law and the measured elapsed amount of time, the number of teeth the oral cleaning device was displaced during the elapsed amount of time; and (iv) determining (850), based on the first location and the number of teeth the oral cleaning device was displaced during the elapsed amount of time, which of the user's teeth were included in the displacement.

15 Claims, 7 Drawing Sheets

(56) References Cited

U.S. PATENT DOCUMENTS

| | | | | |
|---|---|---|---|---|
| 2009/0092955 A1* | 4/2009 | Hwang | ............... | A46B 15/0002 434/263 |
| 2010/0015589 A1* | 1/2010 | Lehavi | ................. | G09B 23/283 434/263 |
| 2012/0310593 A1* | 12/2012 | Bates | ................. | A46B 15/0002 702/150 |
| 2015/0044629 A1* | 2/2015 | Wang | ................. | A46B 15/0006 433/27 |
| 2016/0343270 A1* | 11/2016 | Zheng | ................. | A46B 15/0002 |

FOREIGN PATENT DOCUMENTS

| | | | |
|---|---|---|---|
| RU | 2011141867 | A | 4/2013 |
| WO | 20110733010 | A1 | 6/2011 |
| WO | 2017029570 | A1 | 2/2017 |

* cited by examiner

| V to/from | LLI | LLO | [...] | LRO | LRI |
|---|---|---|---|---|---|
| LLI | P1 | P2 | ... | ... | ... |
| LLO | ... | ... | ... | ... | ... |
| [...] | ... | ... | ... | ... | ... |
| LRO | ... | ... | ... | ... | ... |
| LRI | ... | ... | ... | ... | ... |

FIG. 6

| | | FROM | | | | | | | |
|---|---|---|---|---|---|---|---|---|---|
| | | ULO | ULI | URI | URO | LRO | LRI | LLI | LLO |
| TO | ULO | n/a | R+ | T+ | R+ T+ | R± T- | R- T- | R± | R- |
| | ULI | R- | n/a | R- T+ | T+ | R+ T- | R± T- | R+ | R± |
| | URI | T- | R+ T- | n/a | R+ | R± | R- | R± T+ | R- T+ |
| | URO | R- T- | T- | R- | n/a | R+ | R± | R+ T+ | R± T+ |
| | LRO | R± T- | R- T- | R± | R- | n/a | R+ | T+ | R+ T+ |
| | LRI | R+ T- | R± T- | R+ | R± | R- | n/a | R- T+ | T+ |
| | LLI | R± | R- | R± T+ | R- T+ | T- | R+ T- | n/a | R+ |
| | LLO | R+ | R± | R+ T+ | R± T+ | R- T- | T- | R- | n/a |

FIG. 7

METHODS AND SYSTEMS FOR ORAL CLEANING DEVICE LOCALIZATION

CROSS-REFERENCE TO PRIOR APPLICATIONS

This application is the U.S. National Phase application under 35 U.S.C. § 371 of International Application No. PCT/IB2016/056039, filed on Oct. 8, 2016, which claims the benefit of U.S. Provisional Patent Application No. 62/244,338, filed on Oct. 21, 2015. These applications are hereby incorporated by reference herein.

FIELD OF THE INVENTION

The present disclosure is directed generally to methods and systems for localizing the position of, and tracking movement of, an oral cleaning device using sensor input.

BACKGROUND

Proper tooth brushing technique, including length and coverage of brushing, helps ensure long-term dental health. Many dental problems are experienced by individuals who either don't regularly brush their teeth or who do so inadequately. Among individuals who do regularly brush, improper brushing habits can result in poor coverage of brushing and thus surfaces that are not adequately cleaned.

To facilitate proper brushing technique, toothbrushes have been designed to provide a timer function such that a user knows to brush for a minimum recommended amount of time. The timer function can include an audible sound, haptic feedback, or other notification mechanism to let the user know when a predetermined amount of time has elapsed. This provides the user with an indication that they have brushed their teeth for an adequate amount of time.

Another mechanism to facilitate proper brushing technique is to ensure that there is adequate cleaning of all dental surfaces, including areas of the mouth that are hard to reach or that tend to be improperly cleaned during an average brushing session. One way to ensure adequate coverage is to track the position of the toothbrush in the mouth during a brushing session and compare that to a map of the dental surfaces. For example, a system with sensors positioned in fixed relationship to the teeth of the user could track the movement of a toothbrush over the user's teeth.

Alternatively, the toothbrush could include one or more internal sensors that attempt to track movement of the device within the mouth. In such a system, the user starts with the toothbrush at a known, fixed position within the mouth and subsequent movement of the brush is determined from the one or more internal sensors. However, this approach has several limitations. Users are unable to move their head during brushing as this interferes with the proper positioning of the original fixed reference spot. The system is confused between certain regions of the mouth where data will be similar, such as the upper left inside of the mouth and the upper right outside of the mouth. The resolution of the system is low, meaning that only broad sections of the mouth can be tracked rather than more exact positioning such as teeth.

Accordingly, there is a continued need in the art for a method of tracks the movement of a toothbrush within the mouth using sensor input.

SUMMARY OF THE INVENTION

The present disclosure is directed to inventive methods and systems for tracking movement of an oral cleaning device within the mouth. Applied to a system configured to localize an oral cleaning device within the mouth, the inventive methods and systems enable greater precision of tracking and thus provide an evaluation of a user's brushing technique. The system utilizes a Fitt's law-based model to yield a quantitative measure of human brushing activity in the mouth. According to an embodiment, the Fitt's law-based model allows for a determination of a distance covered within a section of the mouth—and thus the number of teeth brushed—based the amount of time needed to complete the motion, and an observed time. According to an embodiment, the Fitt's law-based model also allows for a determination of a particular transition from one segment of the mouth to another based on the amount of time needed to complete the transition, and an observed time. The system tracks movements and positions over the course of a brushing session, and utilizes that information to provide feedback to a user.

Generally in one aspect, a method for localizing an oral cleaning device within a user's mouth is provided. The method includes the steps of: (i) determining, based on sensor information received from a motion identifier, a first location of the oral cleaning device within the user's mouth; (ii) measuring, using sensor information received from the motion identifier, an amount of time elapsing between a start and a stop of a movement of the oral cleaning device within the user's mouth at the first location; (iii) calculating, using Fitt's law and the measured elapsed amount of time, the number of teeth the oral cleaning device was displaced during the elapsed amount of time; and (iv) determining, based on the first location and the number of teeth the oral cleaning device was displaced during the elapsed amount of time, which of the user's teeth were included in the displacement.

According to an embodiment, the determination of a number of teeth by which the oral cleaning device was displaced during the movement is utilized to determine which of the user's teeth were brushed during the movement.

According to an embodiment, the first location is a section of the mouth.

According to an embodiment, Fitt's law comprises the formula $$W*2^{((MT-a)/b)-1} = D$$

where MT is the elapsed amount of time, W, a, and b are predetermined values, and D is a distance moved within the first location.

According to an embodiment, the method further includes the step of providing calibration data for the oral cleaning device.

According to an embodiment, the calibration data comprises one or more values for W, a, and b.

According to an embodiment, the method further includes the step of evaluating the brushing session. According to an embodiment, the evaluation comprises information about which teeth were cleaned during the brushing session. According to an embodiment, the evaluation comprises information about how well each tooth was cleaned during the brushing session.

According to an aspect is an oral cleaning device. The device includes a motion identifier, and a controller in communication with the motion identifier. The controller is configured to: (i) determine, based on sensor information received from the motion identifier, a first location of the oral cleaning device within the user's mouth; (ii) measure, using sensor information received from the motion identifier, an amount of time elapsing between a start and a stop of a movement of the oral cleaning device within the user's mouth at the first location; (iii) calculate, using Fitt's law and the measured elapsed amount of time, the number of teeth the oral cleaning device was displaced during the elapsed amount of time; and (iv) determine, based on the first location and the number of teeth the oral cleaning device was displaced during the elapsed amount of time, which of the user's teeth were included in the displacement.

According to an aspect is an oral cleaning system. The system includes an oral cleaning device with a motion identifier and a communications module, where the oral cleaning device is configured to transmit, via the communications module, sensor data from the motion identifier. The system also includes a device in communication with the oral cleaning device and comprising a processor, where the processor is configured to: (i) determine, based on sensor information received from the motion identifier, a first location of the oral cleaning device within the user's mouth; (ii) measure, using sensor information received from the motion identifier, an amount of time elapsing between a start and a stop of a movement of the oral cleaning device within the user's mouth at the first location; (iii) calculate, using Fitt's law and the measured elapsed amount of time, the number of teeth the oral cleaning device was displaced during the elapsed amount of time; and (iv) determine, based on the first location and the number of teeth the oral cleaning device was displaced during the elapsed amount of time, which of the user's teeth were included in the displacement.

According to an aspect is a method for localizing an oral cleaning device within a user's mouth. The method includes the steps of: (i) determining, based on sensor information received from a motion identifier, a first location of the oral cleaning device within the user's mouth; (ii) detecting, using sensor information received from the motion identifier, a transition of the oral cleaning device from the first location to a second location within the user's mouth; (iii) calculating, using Fitt's law and an elapsed amount of time for the transition, a probability of which of a plurality of possible transitions occurred during the elapsed amount of time; and (iv) determining, based on the first location and the calculated transition probability, the second location.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

FIG. 6 is a table of transition probabilities in accordance with an embodiment.

FIG. 7 is a table of transitions between various states within the oral cavity in accordance with an embodiment.

DETAILED DESCRIPTION OF EMBODIMENTS

The present disclosure describes various embodiments of a method and controller for tracking the movement and position of an oral cleaning device within the mouth. More generally, Applicant has recognized and appreciated that it would be beneficial to provide a system to track the movement of an oral cleaning device within the mouth in order to provide brushing feedback to the user. Accordingly, the methods described or otherwise envisioned herein provide an oral cleaning device configured to determine the position of the oral cleaning device within the user's mouth and determine, among other variables, how long the user brushes discrete positions within the mouth. According to an embodiment, the method utilizes a Fitt's law-based model to yield a quantitative measure of human brushing activity in the mouth. According to an embodiment, the Fitt's law-based model allows for a determination of a distance covered within a section of the mouth based the amount of time needed to complete the motion, and an observed time.

A particular goal of utilization of the embodiments and implementations herein is to provide brushing information using an oral cleaning device such as an electric toothbrush.

Figure 1:
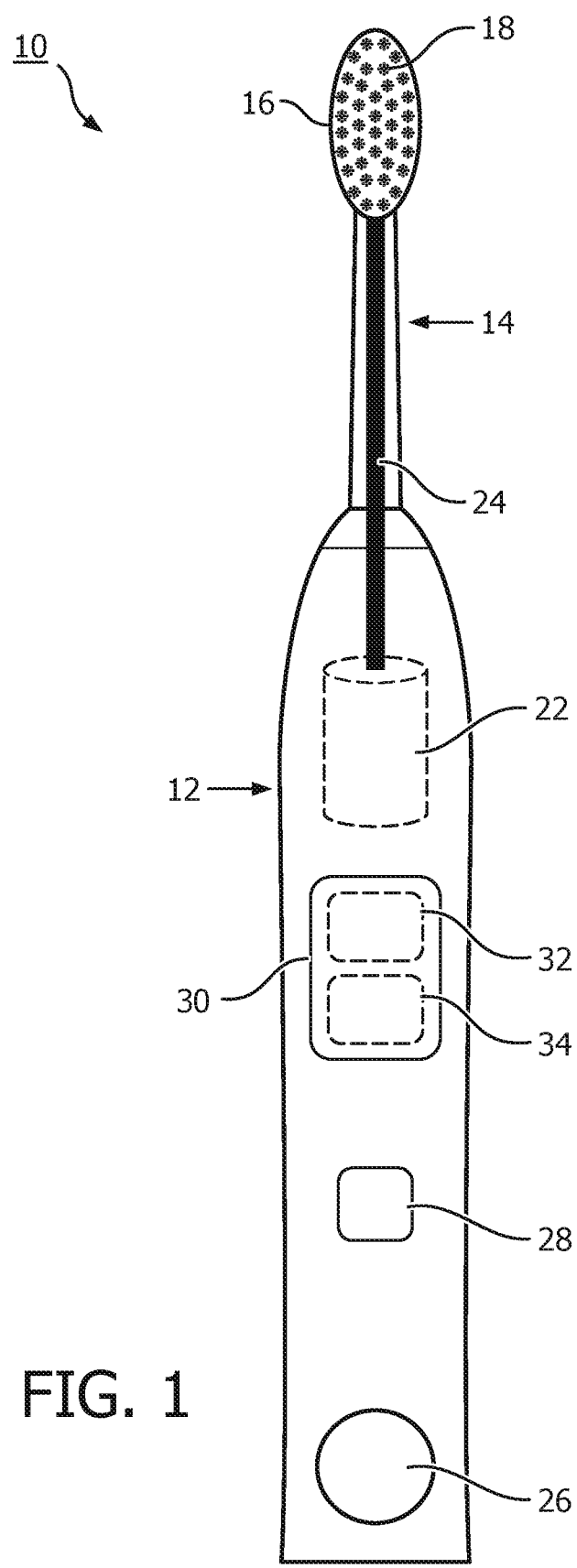
FIG. 1 is a representation of an oral cleaning device in accordance with an embodiment.

Referring to FIG. 1, in one embodiment, an oral cleaning device 10 is provided that includes a body portion 12 and a brush head member 14 mounted on the body portion. Brush head member 14 includes at its end remote from the body portion a brush head 16. Brush head 16 includes a bristle face 18, which provides a plurality of bristles. According to an embodiment, the bristles extend along an axis substantially perpendicular to the head's axis of elongation, although many other embodiments of the brush head and bristles are possible.

According to an embodiment, brush head member 14 is mounted so as to be able to move relative to the body portion 12. The movement can be any of a variety of different movements, including vibrations or rotation, among others.

According to an embodiment, body portion 12 includes a drivetrain 22 for generating movement and a transmission component 24 for transmitting the generated movements to brush head member 14. For example, drivetrain 22 can comprise a motor or electromagnet(s) that generates movement of the transmission component 24, which is subsequently transmitted to the brush head member 14. Drivetrain 22 can include components such as a power supply, an oscillator, and one or more electromagnets, among other components.

Body portion 12 is further provided with a user input 26 to activate and de-activate movement generator 22. The user input 26 allows a user to operate oral cleaning device 10, for example to turn the oral cleaning device 10 on and off. The user input 26 may, for example, be a button, touch screen, or switch.

Although in the present embodiment the oral cleaning device 10 is an electric toothbrush, it will be understood that in an alternative embodiment the oral cleaning device is a manual toothbrush (not shown). In such an arrangement, the manual toothbrush has electrical components, but the brush head is not mechanically actuated by an electrical component.

The oral cleaning device 10 includes one or more motion identifiers 28. Motion identifier 28 are shown in FIG. 1 within body portion 12, but may be located anywhere within the device, including for example within brush head member 14 or brush head 16. The motion identifiers 28 comprise, for example, a 6-axis or a 9-axis spatial sensor system. For example, the motion identifier 28 is configured to provide the readings of six axes of relative motion (three axes translation and three axes rotation), using for example a 3-axis gyroscope and a 3-axis accelerometer. As another example, the motion identifier 28 is configured to provide the readings of nine axes of relative motion using, for example, 3-axis gyroscope, a 3-axis accelerometer, and a 3-axis magnetometer. Other sensors may be utilized either alone or in conjunction with these sensors, including but not limited to a pressure sensor and other types of sensors. Many different types of sensors could be utilized to determine a state and/or transition of the device, as described or otherwise envisioned herein.

The motion identifier 28 is disposed in a predefined position and orientation in the oral cleaning device 10. Therefore, the orientation and position of the brush head member 14 can be easily determined based on the known orientation and position of the motion identifier 28. Accordingly, the brush head member 14 is in a fixed spatial relative arrangement to motion identifier 28.

The motion identifier 28 is configured to generation information indicative of the acceleration and angular orientation of the oral cleaning device 10. The sensor system may comprise two or more motion identifiers 28 that function together as the 6-axis or a 9-axis spatial sensor system. According to another embodiment, an integrated 9-axis spatial sensor can provide space savings in an oral cleaning device 10.

The information generated by the first motion identifier 28 is provided to a controller 30. Controller 30 can comprise a processor 32 and a memory 34. The processor 32 may take any suitable form. For instance, processor 32 may be or include a microcontroller, plural microcontrollers, circuitry, a single processor, or plural processors. Controller 30 may be formed of one or multiple modules, and is operable to operate the oral cleaning device 10 in response to an input, for example user input 26. For example, controller 30 can be configured to actuate a motor control unit. According to an embodiment, the motion identifier 28 is integral to the controller 30. Controller 30 may also comprise, or be in communication with, a clock and/or timer configured to measure one or more amounts of time, as set forth in greater detail below.

Memory 34 can take any suitable form, including a non-volatile memory and/or RAM. The non-volatile memory may include read only memory (ROM), a hard disk drive (HDD) or a solid state drive (SSD). The memory can store, among other things, an operating system. The RAM is used by the processor for the temporary storage of data. The operating system may contain code which, when executed by controller 30, controls operation of each of the hardware components of the oral cleaning device 10.

Figure 2A:
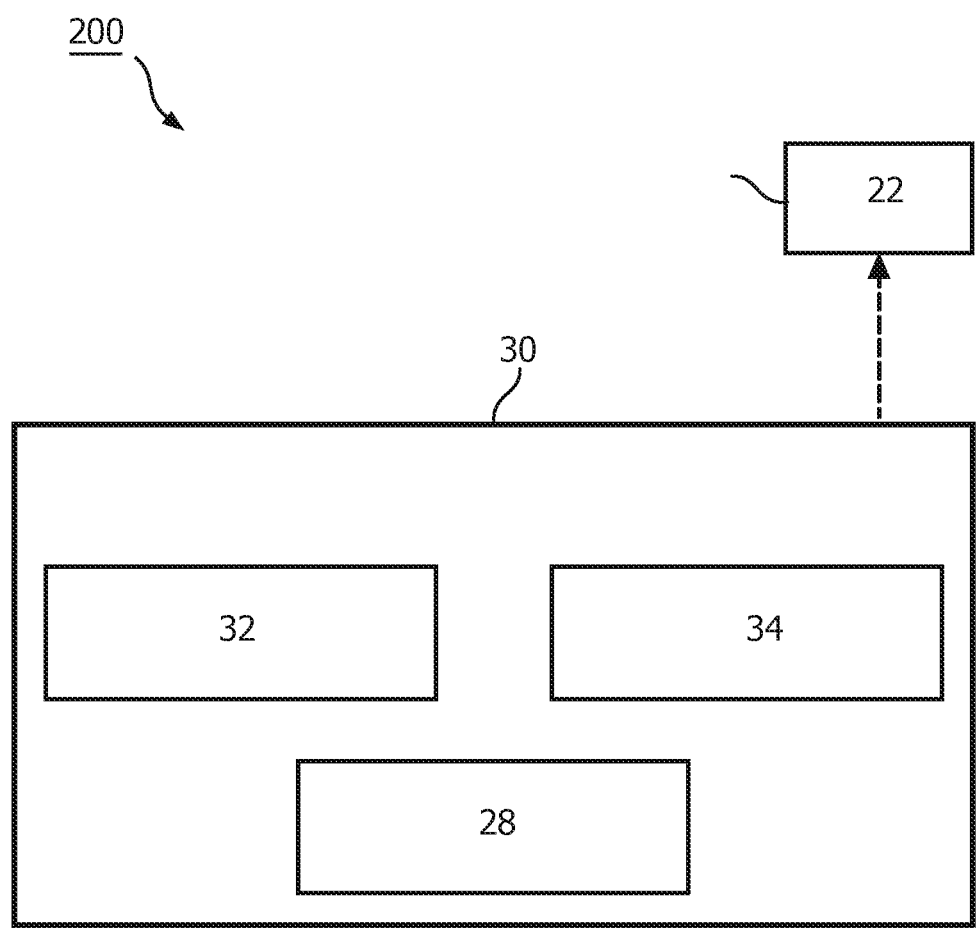
FIG. 2A is a schematic representation of an oral cleaning device control system in accordance with an embodiment.

Referring to FIG. 2A, an embodiment of an oral cleaning system 200 is provided. According to an embodiment, oral cleaning system 200 includes one or more motion identifiers 28 and a controller 30 comprising a processor 32 and a memory 34. When utilized with electric cleaning devices, the oral cleaning system 200 includes a drivetrain 22, the operation of which is controlled by controller 30.

Figure 2B:
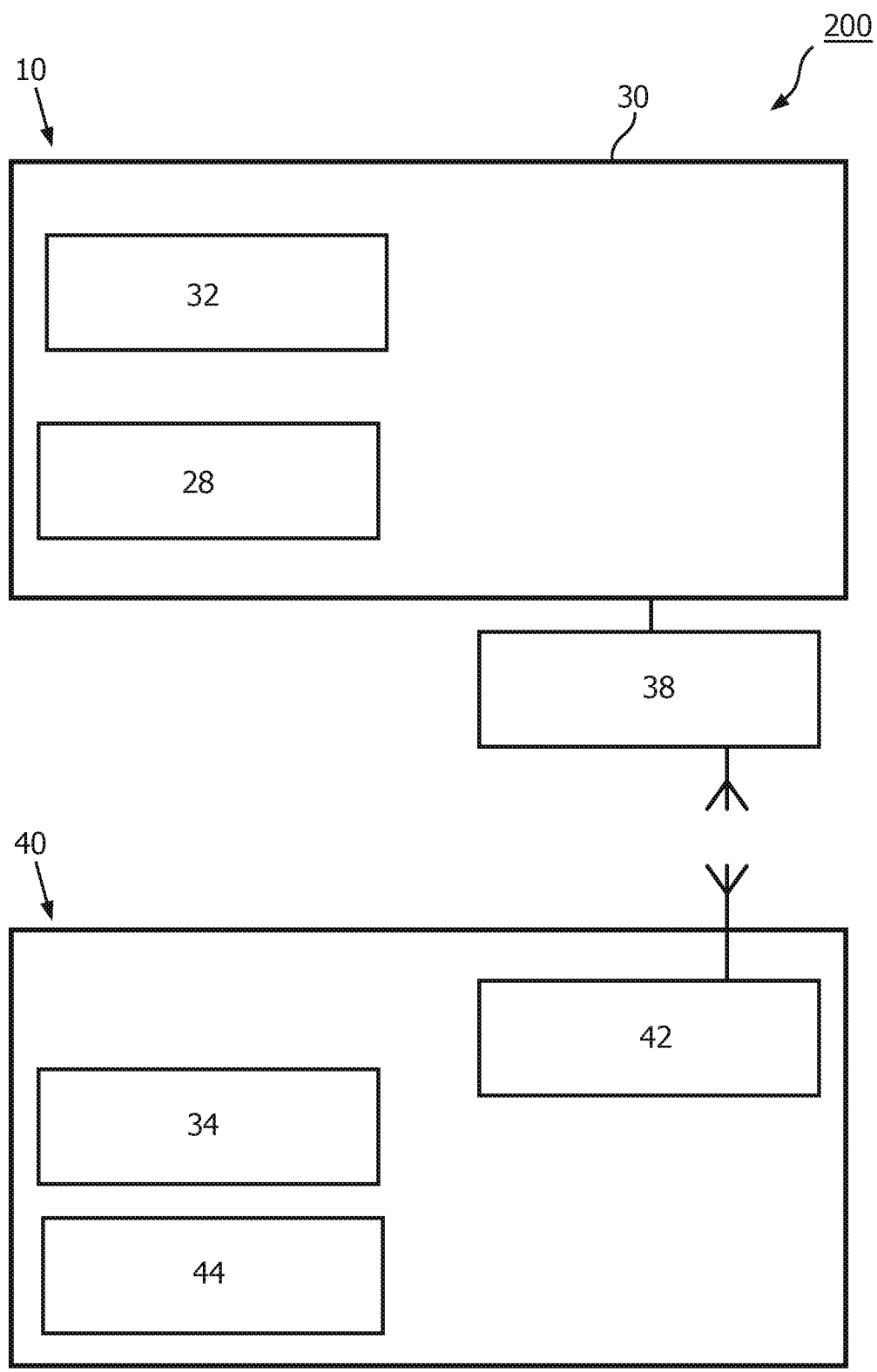
FIG. 2B is a schematic representation of an oral cleaning device control system in accordance with an embodiment.

Referring to FIG. 2B is another embodiment of an oral cleaning system 200 comprising an oral cleaning device 10 and a device 40 which is separate from the oral cleaning device. The oral cleaning device 10 can be any of the oral cleaning device embodiments disclosed or otherwise envisioned herein. According to an embodiment, oral cleaning device 10 includes one or more motion identifiers 28 for spatial sensor information, and a controller 30 comprising a processor 32. The oral cleaning device 10 can include a drivetrain 22, the operation of which is controlled by controller 30.

According to an embodiment, oral cleaning device 10 further comprises a communications module 38 that transmits collected spatial sensor information. The communications module can be any module, device, or means capable of transmitting a wired or wireless signal, including but not limited to a Wi-Fi, Bluetooth, near field communication, and/or cellular module.

According to an embodiment, device 40 can be any device configured to or capable of receiving and processing the spatial sensor information transmitted from oral cleaning device 10. For example, device 40 may be a cleaning device holder or station, a smartphone, a computer, a server, or any other computerized device. According to an embodiment, device 40 includes a communications module 42, which can be any module, device, or means capable of receiving a wired or wireless signal, including but not limited to a Wi-Fi, Bluetooth, near field communication, and/or cellular module. Device 40 also includes a processor 44 which uses the received spatial sensor information from motion identifier 28 to determine and track the position of oral cleaning device 10 as the user moves the device throughout the mouth, as described herein. According to one embodiment, device 40 may include memory 34 to store calibration data, received spatial sensor information, or any other information.

As just one example, oral cleaning device 10 can collect sensor information using motion identifier 28 and transmit that information locally via a Bluetooth connection to a smartphone device 40, where the sensor information is processed and/or stored. As another example, oral cleaning device 10 can collect sensor information using motion identifier 28 and transmit that information via a WiFi connection to the Internet where it is communicated to a remote server device 40. The remote server device 40 processes and/or stores the sensor information. A user may access that information directly or may receive reports, updates, or other information from the remote server device 40 or an associated device.

According to an embodiment, the controller 30 of the oral cleaning device 10 and/or a controller of a remote device 40 also uses sensor information from motion identifier 28 to determine and track the position of oral cleaning device 10 using a Probabilistic Graphical model, such as the Hidden Markov Model ("HMM") or any other Probabilistic Graphical model or hybrid method, to estimate the location of oral cleaning device 10 from spatial sensor information received from motion identifier 28. Positions within the mouth have a specific designation, and each of these designations can be seen as a distinct position of the brush head of the oral cleaning device 10. For example, the approximate position of the brush head in the mouth is called a state. Although according to some embodiments the state may be the exact position of the brush head on a tooth, or more specifically on a specific part of a tooth, the state can be more broadly a segment or section of the mouth, such as upper left outside, upper left inside, and others (see Table 1). As the user moves between different states within the mouth, movement information is generated by motion identifier 28 and sent to controller 30. The Probabilistic Graphical model creates a best estimate for a current state, where the current state probability distribution is calculated from a previous state probability distribution and the probabilities of transitioning from one state to any other state as detected by the motion identifier 28. Thus, the most likely location of the device within a given space is determined based on previous state probability distributions combined with transition probability distributions, where the distributions are one or more matrices which contain the information about the likelihood of transitions between states. There can be multiple transition matrices involved, such as a statistical matrix which contains behavioral information such as how likely a transition is, based on calibration by the user, and a matrix containing the likelihood of a transition having happened based on sensor readings, and/or a matrix containing the likelihood of a transition having happened based on prior knowledge of the system.

According to an embodiment, the controller 30 of the oral cleaning device 10 and/or a controller of a remote device 40 utilizes sensor information from motion identifier 28 for high resolution tracking of the oral cleaning device within the user's mouth. According to an embodiment, the system is configured to measurement position and movement with tooth-by-tooth resolution. The system utilizes a Fitt's law-based model to determine a distance covered by a user within a section of the mouth—and thus the number of teeth brushed—based the amount of time needed to complete the motion, and an observed time. Fitt's law predicts that the time required to move to a target area is a function of the ratio between the distance to the target and the width of the target, using the following equation:

$$MT = a + b * \log_2(2D/W) \tag{Eq. 1}$$

where MT is movement time, or the average time to complete a movement, which can be measured by a clock component of the system. Additionally, a and b are model parameters, and can be determined either in development or during calibration of the device. For example, a and b might be values that are predetermined factory setting depending on the intended user of the device, such as adult versus child, and/or male versus female. As another example, a and b might be values that are determined during a calibration session where the user conducts a directed brushing session. The data obtained during the calibration session can optionally be processed and stored, and model parameters a and b can be determined and set. D is the distance from the starting point to the center of the target, and according to an embodiment is the outcome of the prediction. W is the width of the target measured along the axis of motion. For example, W can be the allowed error tolerance in the final position, since the final point of the motion must fall within ±W/2 of the target's center. According to an embodiment, W can be approximately the size of a human tooth. Accordingly, W may be based at least in part on an intended user of the device, such as adult versus child, and/or male versus female.

According to an embodiment, Equation 1 can be modified to:

$$(MT-a)/b = \log_2(2D/W) \tag{Eq. 2}$$

$$2^{((MT-a)/b)} = 2D/W \tag{Eq. 3}$$

$$W * 2^{((MT-a)/b)-1} = D \tag{Eq. 4}$$

Accordingly, where parameters W, a, and b are known, Equation 4 allows estimation of a moved distance D when a time MT is observed.

According to an embodiment, system 200 utilizes the higher-resolution location information obtained by the Fitt's law-based model alone or in combination with the lower-resolution location information obtained using the Probabilistic Graphical model. For example, once a particular state, segment, or other higher-level measurement of a location within the mouth is identified, that information can be augmented with more specific tooth-by-tooth information obtained using the Fitt's law-based model.

Figure 3:
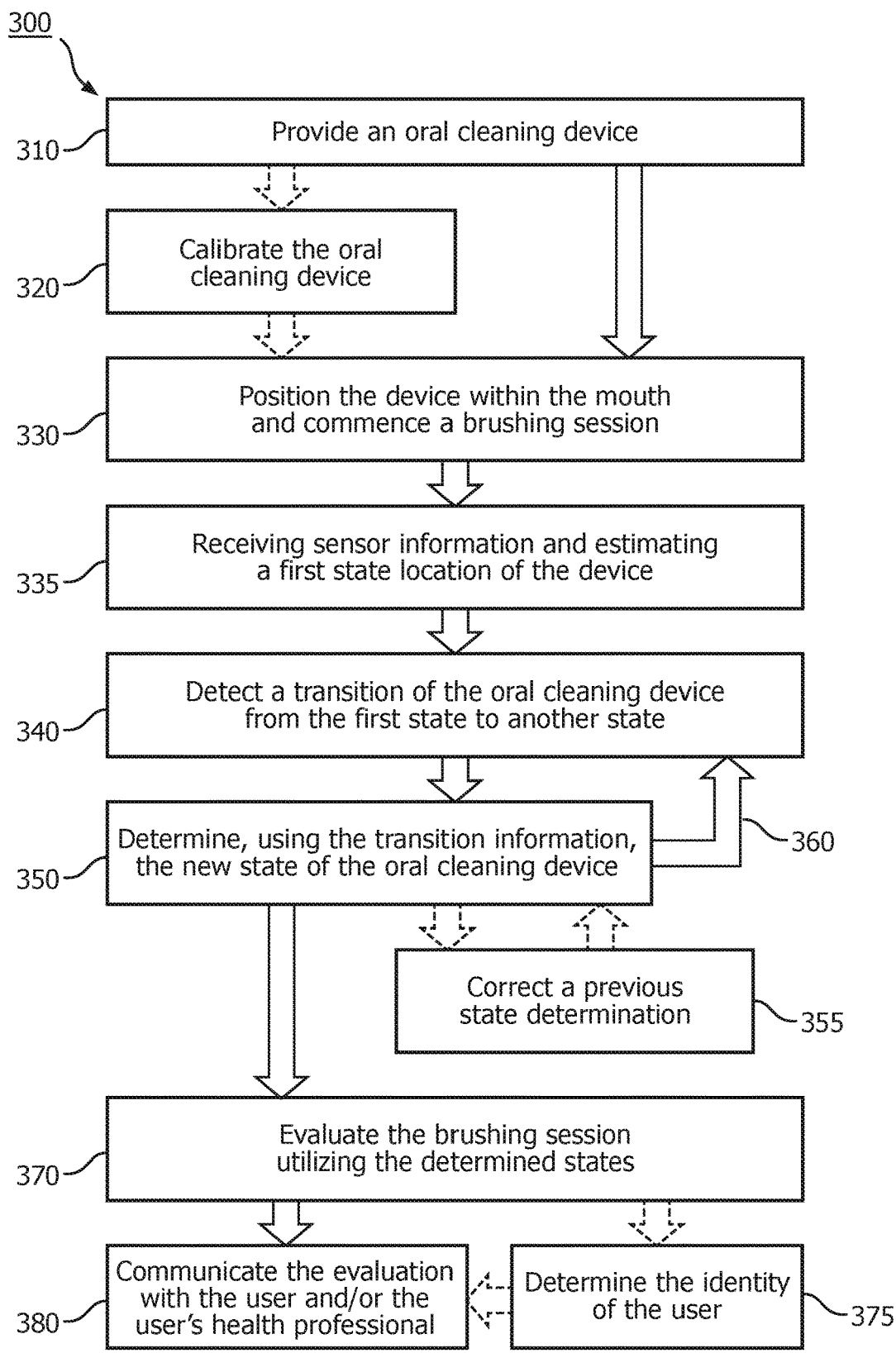
FIG. 3 is a flowchart depicting a method for tracking movement of an oral cleaning device within the mouth using spatial sensor input in accordance with an embodiment.

Referring to FIG. 3, in one embodiment, is a flowchart of a method 300 for tracking movement of a device within a given space. At step 310 of the method, an oral cleaning device 10 is provided. The oral cleaning device can be any of the embodiments described or otherwise envisioned herein. For example, according to one embodiment, oral cleaning device 10 includes a body portion 12, a brush head member 14 with a bristle face 18, a motion identifier 28, and a controller 30 with processor 32 and memory 34. Many other embodiments of the oral cleaning device 10 are also possible.

At optional step 320 of the method, the oral cleaning device 10 can be calibrated. The calibration can comprise, for example, defining positions and/or transitions within the system, which can be done at the factory or by the user. State calibration data consists of annotated sensor data sets. During a calibration session, for example, a designated area is brushed and the instantaneous sensor data is annotated and stored.

According to an embodiment, the calibration can be performed by the individual user since the jaw is unique. This can be performed in several ways. For example, the user can simply use the device and the system can reconstruct a map of the jaw by registering shapes and boundary conditions such as the turning point at the back molars. According to another user calibration method, the user is guided through a brushing session in which it is indicated where he should brush such that the system can map the location to its sensor data as well as train the system to the user's motion pattern (e.g., fast or slow transitions).

According to an embodiment, the calibration step is omitted. Instead, the oral cleaning device develops a calibration data set over one or more brushing sessions by comparing data between those sessions. A self-learning method could also be utilized to supplement, amend, or otherwise adjust a factory or user calibration.

At step 330 of the method, the oral cleaning device is positioned within the mouth at a first location, and the user starts brushing his teeth.

At step 335 of the method, the system determines a probability of a first state using a Probabilistic Graphical model. According to an embodiment, the model will determine a current state probability utilizing the previous state probability, the current state probability based on calibration data, and the probability of transitioning from a previous state to the current state, according to the formula:

$$P(s)=P(s_{cal}) \cdot (P(s_{-1})P(T))  \quad \text{(Eq. 5)}$$

where P(s) is the current state probability matrix, $P(s_{-1})$ is the previous state probability matrix, P(T) is the probability matrix of transitioning from each state s−1 to state s, and $P(s_{cal})$ is the current state probability matrix based on calibration data from step 320. The resulting distribution is then normalized.

However, during estimation of the first position within the user's mouth there will not be a previous location probability. Accordingly, for estimation of the first position only calibration data can be utilized to determine the location. There are several methods for current state estimation, and these are provided in greater detail below. For example, according to an embodiment, the probability of the first, unknown, state is determined based on the calibration data, while subsequent unknown states are determined using the equation $P(s)=P(s_{-1})*P(T)$.

According to an embodiment, a transition matrix T provides the probability of transitioning from each possible state to every other possible state.

The matrix is then multiplied by the current state matrix S. In the example, the current state was 100% accurately known, but this is not necessarily the case. The current position is mostly uncertain as well, leading to a matrix S with a probability distribution. The result of the multiplication of transition probabilities and state probabilities gives us the new state probability distribution matrix P. From this matrix P the most likely current state can be determined, and used to provide feedback to the user.

$$\begin{bmatrix} T_{1,1} & T_{2,1} & T_{3,1} \\ T_{1,2} & T_{2,2} & T_{3,2} \\ T_{1,3} & T_{2,3} & T_{3,3} \end{bmatrix} \times \begin{bmatrix} S_1 \\ S_2 \\ S_3 \end{bmatrix} = \begin{bmatrix} P_1 \\ P_2 \\ P_3 \end{bmatrix} \quad \text{(Eq. 6)}$$

The transition matrix T itself can be the result of a multiplication of probabilities, and can also comprise probability information of behavioral patterns. For instance, it is unlikely that a user would skip a single tooth while brushing. For example, a transition from tooth #1 to tooth #3, while completely skipping tooth #2 between them, is unlikely. There is a transition probability between each two teeth, which can be incorporated into the transition matrix T. These behavioral probabilities can be obtained by, for example, a guided calibration session, or data mined from consumer studies.

According to an embodiment, the transition matrix T comprises boundary condition information. Since the shape of a jaw is known, boundary conditions can be imposed on the calculation. For example, if the system is tracking the absolute position on the jaw and information from the motion indicator suggests that a new position is located five centimeters outside the jaw, then that is assigned a negligible probability, since the estimated location does not fall within the system boundaries. At such a moment, the tracking might be considered lost until the estimated new location falls back within the boundary conditions of the system or a second position, lying within the boundaries of the system, also has a high probability of being the true location. Whenever the tracking is lost and found again, the intermediate path can be backtracked from the newly found position, using the transition probabilities that occurred while the trace was lost.

According to an embodiment, the instantaneous sensor values can already give an indication of location, before transition probabilities are considered. Each combination of sensor data already restricts the likely position. For example, when the brush is pointing inwards, the brush is located at the outside of the jaw, which excludes certain states. These observations can also help to recover a lost position tracking. The model which links the states to instantaneous sensor data can be data mined from calibration steps, either by the end-user or during development.

At step 340 of the method, a transition occurs and is detected by information from the motion identifier 28. For example, the motion identifier may detect a translation from one side of the mouth to the other side, a rotation from the inside of the mouth to the outside of the mouth, or both a translation and a rotation. The gyroscope, accelerometer, magnetometer, pressure sensor, and/or other sensors of the motion identifier 28 send information to the controller 30 continuously or periodically, and a change in that information can be interpreted by the system as a transition, including but not limited to a translation, rotation, and/or other movements or transitions. According to an embodiment, the controller interprets the information form the motion identifier 28 as a transition based on comparison to calibration data, comparison to pre-determined or preprogrammed data, and/or other data.

Once a transition is complete, the controller 30 will utilize that information to determine, at step 350 of the method, the new location, or state, of the oral cleaning device 10 in the mouth. Accordingly, unlike previous methods, a state is determined only after the transition of the device from the previous state to the current state is complete. To determine the new state, the controller compares the transition information from the motion identifier 28 to the calibration data. For example, the controller can determine how well the new data compares to calibration points and obtains a measure of similarity. As described below in detail, there are multiple ways to accomplish step 350 by comparing the transition information from the motion identifier 28 to the calibration data, including: (i) a histogram correlation; (ii) a probability density distribution analysis; and/or (iii) a nearest neighbor analysis.

For the histogram correlation approach, a normalized histogram is built for one or more axes of both the calibration data and currently observed sensor data from the motion identifier 28. Correlation is calculated by the inner product of the histograms, with element-wise multiplication and then summation. The data set with the most matching data points will lead to the highest sum. When multiple axes are used, the total estimation is calculated by multiplying the results of the individual axes.

For the probability density distribution analysis, a normal distribution function is fit to the calibration dataset using the following equation:

$$f(x \mid \mu, \sigma) = \frac{1}{\sigma\sqrt{2\pi}} e^{-\frac{(x-\mu)^2}{2\sigma^2}} \quad \text{(Eq. 7)}$$

The current position is then estimated by finding the probability of each individual point of the observed sensor data in the probability density distribution. According to an embodiment, this approach is less sensitive to possible gaps in the calibration data, for example.

Some state observations lead to ambiguous results in localization. In order to distinguish between these states, it is necessary to look at the transition(s) that led to the state. The most distinctive characteristic of a transition in mouth can be, for example, the angular displacement between a first and second state. However, each transition only corresponds to one set of displacements (x, y, and z). Therefore, there may not be sufficient data to build a normal probability distribution to compare with a calibration set. Due to the small number of data points, the nearest neighbor analysis can be utilized. According to an embodiment, when a transition is observed, the system looks for the five nearest (dx, dy, dz) neighbors of the transition, although less than five or more than five may be utilized in other embodiments. Preferably the system looks for a number of neighbors that would avoid equal odds. The probability of each transition is determined by the number of nearest neighbors each cluster contributed.

Therefore, according to an embodiment, for the nearest neighbor analysis the observed sensor data from the motion identifier 28 is compared the calibration data set by looking at the x number of nearest neighbor in multi-dimensional space. The distance between a measured point—as determined by the observed sensor data from the motion identifier 28—and each calibration point is calculated by taking the norm of the difference between points represented as two vectors in three-dimensional space:

$$d=\|\vec{a}-\vec{b}\|\quad\quad\quad\text{(Eq.8)}$$

The probability for each position can then be calculated by the relative number of nearest neighbors being assigned to that position, using for example the following equation where n(total) is the total number of neighbors taking into account:

$$P(s)=n(s)/n(\text{total})\quad\quad\quad\text{(Eq. 9)}$$

Figure 4:
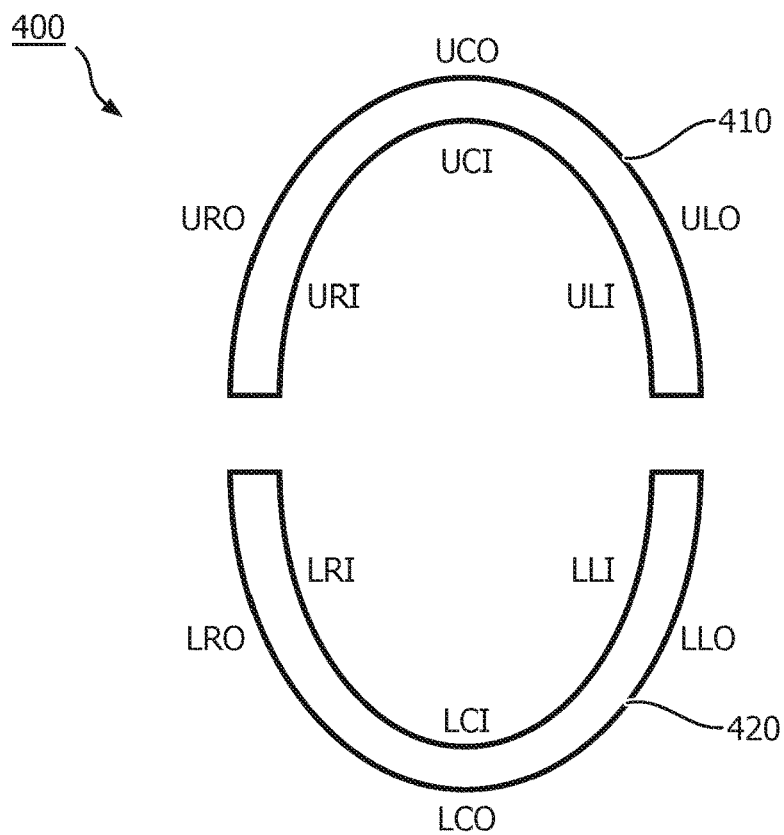
FIG. 4 is a schematic representation of various states within the oral cavity in accordance with an embodiment.

According to an embodiment, states and transitions in the dental cavity can be clearly defined, including but not limited to by calibration data. Referring to FIG. 4, in accordance with an embodiment, are defined states for the mouth. The mouth 400 includes upper teeth 410 and lower teeth 420 with states defined as set forth in TABLE 1. These can also be identified as sections of the mouth. A transition is a movement from any one of the states to any other of the states. Some transitions are clear while others are ambiguous, as set forth in greater detail below. Additionally, some transitions are more likely to occur while others are less likely to occur, and this information could optionally be a component of the analysis.

TABLE 1

State Abbreviations

| State Abbreviation | State Full Name |
|---|---|
| LLI | Lower left inside |
| LLO | Lower left outside |
| ULO | Upper left outside |
| ULI | Upper left inside |
| URI | Upper right inside |
| URO | Upper right outside |
| LRO | Lower right outside |
| LRI | Lower right inside |
| LCI | Lower center inside |
| LCO | Lower center outside |
| UCO | Upper center outside |
| UCI | Upper center inside |
| LCI | Lower center inside |

Figure 5:
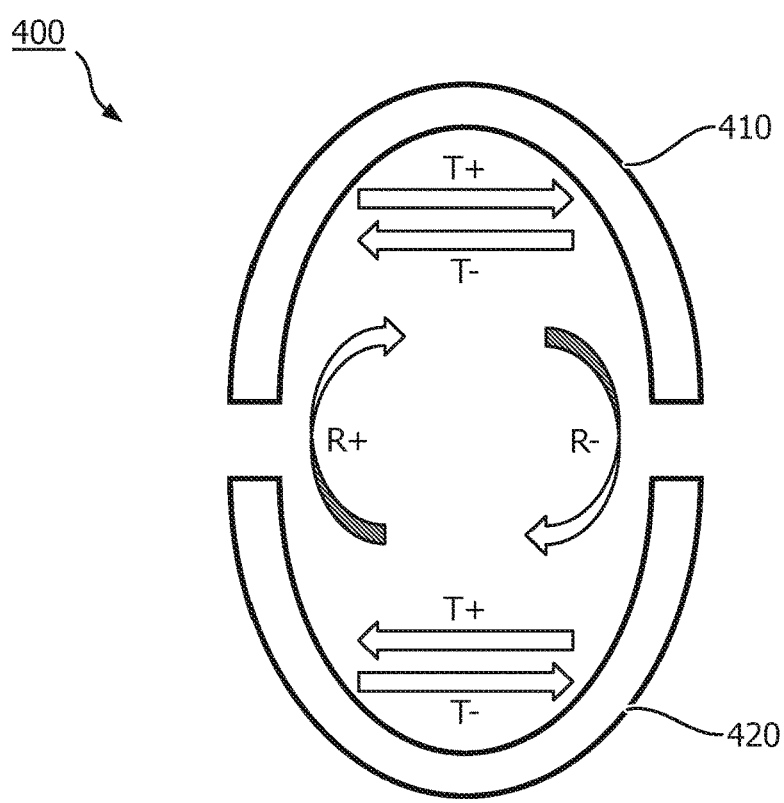
FIG. 5 is a schematic representation of transitions between various states within the oral cavity in accordance with an embodiment.

Referring to FIG. 5, in accordance with an embodiment, are defined transitions between states in the mouth. The mouth 400 includes upper teeth 410 and lower teeth 420 with transitions defined as either a positive or negative translation ("T") and/or a positive or negative rotation ("R"). Some transitions involve only one type of motion (T or R), while other transitions involve two types of motion (T and R).

According to an embodiment, the transition probability can be visualized as a table, where an observed signal such as a set of accumulated angle changes provides a probability of each possible transition being true. This can be done fully probabilistically, and/or based on a set of rules.

The Probabilistic Method

According to an embodiment, the fully probabilistic method requires a full calibration set of sensor data, which according to an embodiment is angular rotation. After detecting a transition, the sensor rotation between before and after transition is compared to the calibrated angular rotation for each possible transition by one of the above methods for the state estimate, resulting in a table as shown in FIG. 6. For each state transition, indicated by a To/From such as LLO (lower left outside) to LLI (lower left inside), for example, there is a probability P2 that the possible transition is true.

The Rule-Based Method

According to an embodiment, the rule-based method is based on prior knowledge of the system, where the type of motion between each segment is known. A table is made with type of motion that can be defined, in this case left and right translations (T+/−), left and right rotations (R+/−), and/or 180° rotations, as shown in FIG. 7. According to an embodiment, the calibration set can contain only calibration data (e.g. angular rotations) for each type of motion.

When a transition is detected, the angular rotation signatures are compared to the existing signatures, in this example using the nearest-neighbor approach, to assign a probability of each motion being observed. These normalized probabilities are assigned to the corresponding positions in the table, where the motion is expected to occur. All positions where the motion is not expected get assigned the inverse of the probability. According to an embodiment, this results in one full table for each possible motion.

For example, when the positive rotation R+ is observed with a 0.6 certainty, each element in the R+ table where R+ occurs gets assigned 0.6. All other elements are assigned (1−0.6), because this is the chance of any of the others being true when R+ is NOT observed.

According to an embodiment, all tables are then multiplied element-wise to get the final transition probability distribution. When a movement is not observed, each element is assigned the same value (1/N), so the table does not influence the relative odds in the end. According to an embodiment, the representation does not need to be individual tables. It could also be performed using libraries, look-up tables, or other methods.

Returning to Equation 5, above, the probability of being in a certain state, P(s), is equal to the sum of the odds given by all combinations of having started at any other state, P(s-j), and transitioning to that specific location with probability, P(T). To resolve ambiguities and arrive at a better estimate, the estimate is multiplied again by the current state probability based on the calibration data, $P(s_{cal})$.

According to an embodiment, resolution of ambiguity requires origin information $P(s_{-1})$, transition information P(T), and destination information $P(s_{cal})$. This is because, for example, for some positions, a state detected in the dental cavity could be a minimum of two different states. For example, ULO and URI might be indistinguishable until a transition occurs, and even then some transitions may be indistinguishable. A ULO to ULI or a ULI to ULO transition, for example, comprises a rotation, but it might be difficult for the system to determine the exact positioning, at least until an asymmetry is introduced. As soon as there is a distinguishable transition, caused by the asymmetry, then the system is free of the ambiguity. Typically, the system will not only be free of the ambiguity but will be able to determine the previous state that was previously ambiguous.

At optional step 355 of the method in FIG. 3, according to an embodiment, one or more previous state determinations are corrected. For example, a state determination may be determined at step 350 of the method, but a subsequent transition may indicate that the previous state transition was incorrect. For example, the subsequent transition may be either impossible or unlikely from the incorrectly determined state, which may trigger a review and/or possible correction. The system can utilize one or more previous transitions, along with the most recent transition, to determine and correct the incorrectly determined state.

Similarly, the system can determine a current state and/or correct a previous state if the system momentarily loses track of either a state or transition, or is unable to recognize a state or transition. For example, the system may determine using previous sensor information that it is at a hypothetical state S1, followed by an undeterminable transition T? to a new undeterminable state S?. A subsequent known transition T2 results in determined state S3, which means that the previous undeterminable transition T? to state S? must have been a transition T1 to state S2. The obtained information can be utilized for self-learning and/or to refine or otherwise define the calibration data set.

Thus, at step 360 of the method in FIG. 3, the system detects a second transition of the oral cleaning device from one state to another state. For example, the motion identifier may detect a translation from one side of the mouth to the other side, a rotation from the inside of the mouth to the outside of the mouth, or both a translation and a rotation. The gyroscope, accelerometer, magnetometer, and/or other sensors of the motion identifier 28 send information to the controller 30 continuously or periodically, and a change in that information can be interpreted by the as a transition, including but not limited to a translation, rotation, and/or other movements or transitions. According to an embodiment, the controller interprets the information form the motion identifier 28 as a transition based on comparison to calibration data, comparison to pre-determined or preprogrammed data, and/or other data. Steps 340, 350, and 360 may be repeated throughout the course of the brushing session.

According to another embodiment, the method utilizes only transition data to track motion and determine the state of the oral cleaning device. For example, when a transition is detected that necessarily defines the state to which the oral cleaning device was moved or is now located, then only the transition data is necessary. In a scenario where a transition defines two or more possible states, it may be necessary to either rely on other sensor data, or to utilize a previous and/or subsequent transition to determine the previous state.

At step 370 of the method, the system utilizes the state determinations, or just the transition data as described above, obtained during a brushing session to evaluate the brushing session. According to an embodiment, the system stores information about the state determinations obtained during a brushing session in order to create or otherwise perform the evaluation, either now or at some point in the future. According to another embodiment, the system stores information about multiple brushing sessions to accumulate data over time, including improvement in brushing times, technique, or other metric, as well as lack of improvement.

For example, one goal of the evaluation of the brushing session can be to track the amount of time the user spends brushing each location. If the total recommended brushing time is two minutes, for example, each of the twelve regions identified in FIG. 4 should be brushed for approximately ten seconds. The system can compare the tracked states to a timer, clock, or table to determine which regions were adequately brushed and which regions were not adequately brushed.

According to an embodiment, the system could utilize other evaluation metrics for the brushing session. For example, another metric could be distance travelled within each region. This might require knowledge of the size of the jaw which could be extracted, for example from either a calibration session or normal brushing. Another metric could be the spread of signals within a single region. For example, if the user is keeping the brush in one location only, the spread will be very small. When the user is moving in one region, thus covering it more completely, the spread will be larger and more conforming to the calibration curves, which are also wider. According to an embodiment, the system can utilize multiple metrics to evaluate a brushing session in a multi-dimensional manner.

At optional step 375 of the method, the system determines who was using the brush during the brushing session. The system can then optionally associate the information with a user and/or user account. For example, according to an embodiment, the system uses the observed order of determines states to determine who was using the brush during the brushing session. It can be reasonably assumed that most users will brush their teeth in identical or similar patterns during brushing sessions. Accordingly, once a determined order or pattern is associated with a particular user and/or user account, subsequent brushing sessions that are sufficiently close to the stored or associated order or pattern. The determination of whether a session is sufficiently close to a prior session may be determined by a threshold or a probability determination, for example.

At step 380 of the method, the evaluation of the brushing session can be communicated. For example, the system could communicate information to the user about which regions were adequately brushed and which regions were not adequately brushed. This could be performed utilizing a display, such as a display with eight or twelve target regions and a visual indicator of which regions were adequately brushed, which regions were not adequately brushed, and/or both. According to an embodiment, the system can provide real-time tracking and localization data to a user or to a remote system. For example, the system can transmit real-time tracking and localization data to a computer via a wired or wireless network connection. As another example, the system can transmit stored tracking and localization data to a computer via a wired or wireless network connection. Thus, the system could transmit information about a single brushing session and/or multiple brushing sessions directly to a healthcare professional such as a dentist or dental hygienist.

Figure 8:
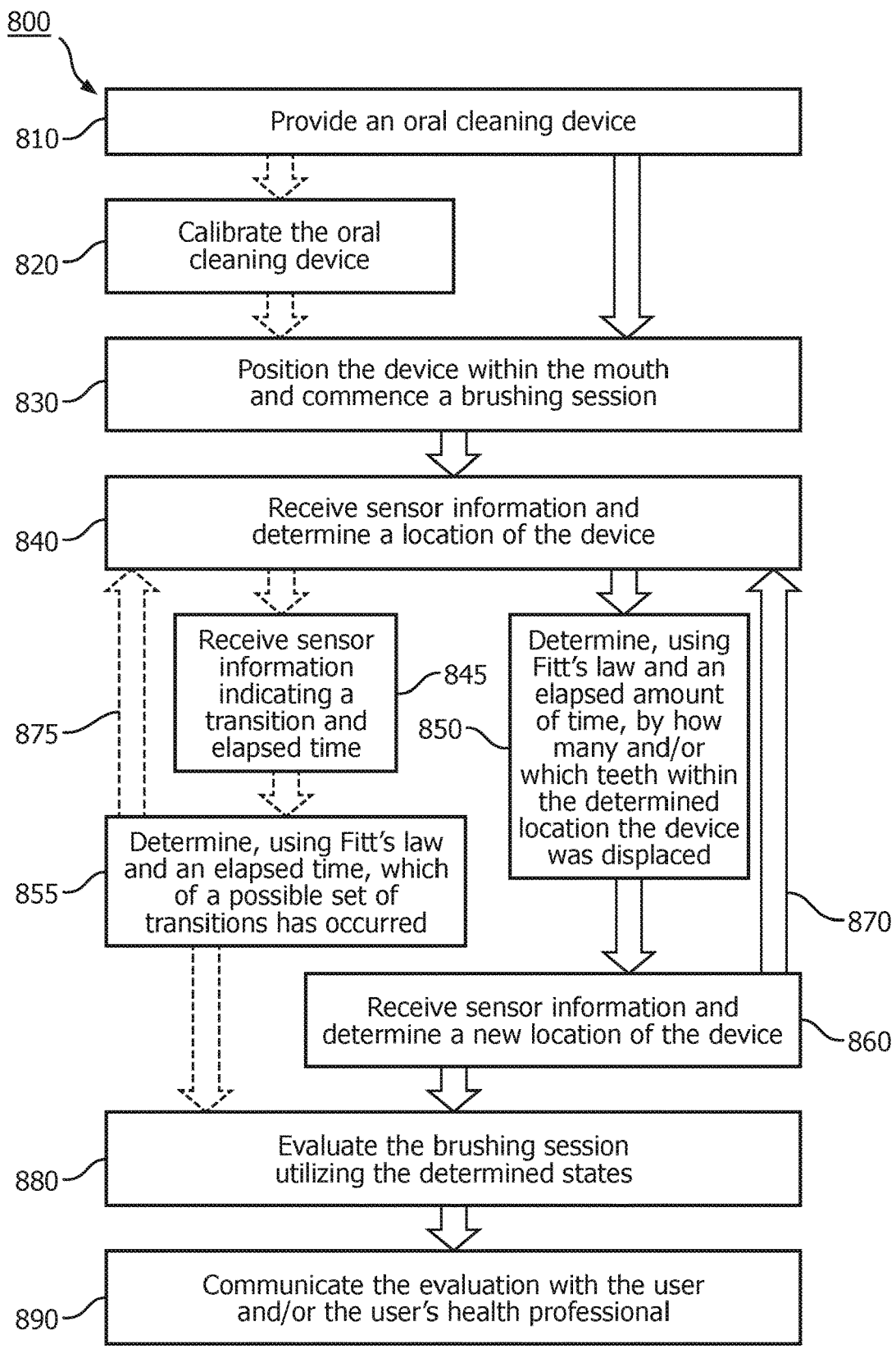
FIG. 8 is a flowchart depicting a method for tracking movement of an oral cleaning device within the mouth using spatial sensor input in accordance with an embodiment.

Referring to FIG. 8, in one embodiment, is a flowchart of a method 800 for tracking movement of a device within a given space using a Fitt's law-based model. At step 810 of the method, an oral cleaning device 10 is provided. The oral cleaning device can be any of the embodiments described or otherwise envisioned herein. For example, according to one embodiment, oral cleaning device 10 includes a body portion 12, a brush head member 14 with a bristle face 18, a motion identifier 28, and a controller 30 with processor 32 and memory 34. Many other embodiments of the oral cleaning device 10 are also possible.

At optional step 820 of the method, the system 200 can be calibrated. The calibration can comprise, for example, defining variables W, a, and/or b, which can be done at the factory or by the user. During a calibration session, for example, a designated area is brushed and the instantaneous sensor data is annotated and stored. According to an embodiment, the calibration can be performed by the individual user since the jaw is unique. This can be performed in several ways. For example, the user can simply use the device and the system can reconstruct a map of the jaw by registering shapes and boundary conditions such as the turning point at the back molars. According to another user calibration method, the user is guided through a brushing session in which it is indicated where he should brush such that the system can map the location to its sensor data as well as train the system to the user's motion pattern.

According to an embodiment, the calibration step is omitted. Instead, the oral cleaning device develops a calibration data set over one or more brushing sessions by comparing data between those sessions. A self-learning method could also be utilized to supplement, amend, or otherwise adjust a factory or user calibration.

At step 830 of the method, the oral cleaning device is positioned within the mouth at a first location, and the user starts brushing his teeth.

At step 840 of the method, the motion identifier 28 obtains sensor data and the system utilizes the sensor data to determine an approximate location of the device within the mouth. The approximate location is a state, segment, or other higher-level measurement of a location within the mouth. According to an embodiment, the system utilizes the Probabilistic Graphical model described or otherwise envisioned herein to determine what portion of the mouth is being brushed, including but not limited to the positions set forth in TABLE 1. Other methods of identifying the state, segment, or other higher-level measurement of a location within the mouth are also possible.

At step 850 of the method, using information about the approximate location of the device in the mouth, the system can use the Fitt's law-based model to determine a number of teeth that the device was displaced using equation 4:

$$W*2^{((MT-a)/b)-1} = D \quad \text{(Eq. 4)}$$

where parameters W, a, and b are known and MT is an observed amount of time. The observed time MT can be obtained by measuring the amount of time between when a motion is started and ended, where the motion is detected by motion identifier 28. The measured time MT is correlated to the number of teeth between the start and end of the motion, since the number of teeth covered in one motion is exponentially related to the time needed to complete the motion.

According to an embodiment, the information about the number of teeth between the start and end of the motion, i.e., the number of teeth that the device was displaced, can be utilized by the system for different purposes. For example, the information can be used to determine which teeth were being cleaned during the motion. According to another embodiment, the information can be used to trigger an action by the oral cleaning device, such as affecting the device's air flow, fluid dispersal, or a variety of other actions.

At step 860 of the method in FIG. 8, the system determines a second location of the oral cleaning device 10 within the mouth. For example, according to an embodiment the motion identifier may detect a translation from one side of the mouth to the other side, a rotation from the inside of the mouth to the outside of the mouth, or both a translation and a rotation. The gyroscope, accelerometer, magnetometer, and/or other sensors of the motion identifier 28 send information to the controller 30 continuously or periodically, and a change in that information can be interpreted by the as a transition, including but not limited to a translation, rotation, and/or other movements or transitions. According to an embodiment, the controller interprets the information form the motion identifier 28 as a transition based on comparison to calibration data, comparison to pre-determined or preprogrammed data, and/or other data. Steps 850, 860, and 870 may be repeated throughout the course of the brushing session.

According to another embodiment of the method, which can be utilized alone or in conjunction with the steps above, the Fitt's law-based model is utilized to determine which of a plurality of possible transitions is likely to have occurred based on received sensor data. For example, at step 845, the motion identifier of the oral cleaning device detects a transition from one section of the mouth to another section of the mouth. For example, the motion identifier may detect a translation from one side of the mouth to the other side, a rotation from the inside of the mouth to the outside of the mouth, or both a translation and a rotation. The gyroscope, accelerometer, magnetometer, and/or other sensors of the motion identifier 28 send information to the controller 30 continuously or periodically, and a change in that information can be interpreted by the as a transition, including but not limited to a translation, rotation, and/or other movements or transitions.

At step 855 of this embodiment of the method, using the sensor information about the detected transition and an observed amount of time for that transition, the system can use the Fitt's law-based model to determine which of a plurality of possible transitions likely occurred using Equation 4, above, where parameters W, a, and b are known and MT is the observed amount of time. The observed time MT is obtained by measuring the amount of time between when a transition is started and when the transition is ended, where the motion is detected by motion identifier 28. The measured time MT is correlated to the type of transition, since the type of transition will be related to the time needed to complete the transition motion. The identified transition can then be utilized for a variety of purposes, including refining other location measurements. According to this embodiment, steps 845, 855, and 875 may be repeated throughout the course of the brushing session.

At step 880 of the method, the system utilizes the brushing information obtained during the brushing session to evaluate the brushing session. According to an embodiment, the system stores information about individual teeth cleaned during a brushing session in order to create or otherwise perform the evaluation, either immediately or at some point in the future. According to another embodiment, the system stores information about multiple brushing sessions to accumulate data over time, including improvement in brushing times, technique, or other metric, as well as lack of improvement.

For example, one goal of the evaluation of the brushing session can be to track the amount of time the user spends brushing each tooth. If the total recommended brushing time is two minutes, for example, each of the approximately 32 individual teeth in an adult should be brushed for approximately 4 seconds. The system can compare the tracked states to a timer, clock, or table to determine which regions were adequately brushed and which regions were not adequately brushed.

At step 890 of the method, the evaluation of the brushing session can be communicated. For example, the system could communicate information to the user about which teeth and/or regions were adequately brushed and which teeth and/or regions were not adequately brushed. This could be performed utilizing a display, such a visual indicator of which teeth or regions were adequately brushed, which teeth or regions were not adequately brushed, and/or both. According to an embodiment, the system can provide real-time tracking and localization data to a user or to a remote system. For example, the system can transmit real-time tracking and localization data to a computer via a wired or wireless network connection. As another example, the system can transmit stored tracking and localization data to a computer via a wired or wireless network connection. Thus, the system could transmit information about a single brushing session and/or multiple brushing sessions directly to a healthcare professional such as a dentist or dental hygienist.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. A method for localizing an oral cleaning device within a user's mouth, the method comprising the steps of:
    determining, based on sensor information received from a motion identifier, a first location of the oral cleaning device within the user's mouth;
    measuring, using sensor information received from the motion identifier, an amount of time elapsing between a start and a stop of a movement of the oral cleaning device within the user's mouth at the first location;
    calculating, using Fitt's law and the measured elapsed amount of time, the number of teeth the oral cleaning device was displaced during the elapsed amount of time; and
    determining, based on the first location and the number of teeth the oral cleaning device wa displaced during the elapsed amount of time, which of the user's teeth were included in the displacement.

2. The method of claim 1, wherein said determination step comprises determining which of the user's teeth were brushed by the oral cleaning device during the movement.

3. The method of claim 1, wherein the first location is a section of the user's mouth.

4. The method of claim 1, wherein said Fitt's law comprises the formula $$W * 2^{((MT-a)/b)-1} = D$$

where MT is the elapsed amount of time, W, a, and b are predetermined values, and D is a distance moved within the first location.

5. The method of claim 4, further comprising the step of providing calibration data for the oral cleaning device, the calibration data comprising one or more values for W, a, and b.

6. The method of claim 1, further comprising the step of evaluating the brushing session.

7. The method of claim 6, wherein said evaluation comprises information about which of the user's teeth were cleaned during the brushing session.

8. An oral cleaning device comprising:
a motion identifier; and
a controller in communication with the motion identifier, wherein the controller is configured to: (i) determine, based on sensor information received from the motion identifier, a first location of the oral cleaning device within the user's mouth; (ii) measure, using sensor information received from the motion identifier, an amount of time elapsing between a start and a stop of a movement of the oral cleaning device within the user's mouth at the first location; (iii) calculate, using Fitt's law and the measured elapsed amount of time, the number of teeth brushed during the elapsed amount of time; and (iv) determine, based on the first location and the number of teeth the oral cleaning device was displaced during the elapsed amount of time, which of the user's teeth were included in the displacement.

9. The oral cleaning device of claim 8, wherein said Fitt's law comprises the formula $$W*2^{((MT-a)/b)-1}=D$$

where MT is the elapsed amount of time, W, a, and b are predetermined values, and D is a distance moved within the first location.

10. The oral cleaning device of claim 8, wherein the controller further comprises calibration data for the oral cleaning device.

11. The oral cleaning device of claim 8, wherein the controller is further configured to evaluate the brushing session.

12. The oral cleaning device of claim 8 further comprising a communications module, wherein the oral cleaning device is configured to transmit, via the communications module, sensor data from the motion identifier; and
a device in communication with the communications module and comprising a processor, wherein the processor is configured to: (i) determine, based on sensor information received from the motion identifier, a first location of the oral cleaning device within the user's mouth; (ii) measure, using sensor information received from the motion identifier, an amount of time elapsing between a start and a stop of a movement of the oral cleaning device within the user's mouth at the first location; (iii) calculate, using Fitt's law and the measured elapsed amount of time, the number of teeth brushed during the elapsed amount of time; and (iv) determine, based on the first location and the number of teeth the oral cleaning device was displaced during the elapsed amount of time, which of the user's teeth were included in the displacement.

13. The oral cleaning device of claim 12, wherein said Fitt's law comprises the formula $$W*2^{((MT-a)/b)-1}=D$$

where MT is the elapsed amount of time, W, a, and b are predetermined values, and D is a distance moved within the first location.

14. A method for localizing an oral cleaning device within a user's mouth, the method comprising the steps of:
determining, based on sensor information received from a motion identifier, a first location of the oral cleaning device within the user's mouth;
detecting, using sensor information received from the motion identifier, a transition of the oral cleaning device from the first location to a second location within the user's mouth;
calculating, using Fitt's law and an elapsed amount of time for the transition, a probability of which of a plurality of possible transitions occurred during the elapsed amount of time; and
determining, based on the first location and the calculated transition probability, the second location.

15. The method of claim 14, wherein a location is a section of the mouth.

* * * * *